United States Patent [19]
Yamasaki et al.

[11] Patent Number: 5,451,664
[45] Date of Patent: Sep. 19, 1995

[54] ACTA AND METHODS FOR DETECTING THE SAME

[75] Inventors: Masahiko Yamasaki; Numa Masayuki, both of Hino, Japan

[73] Assignee: Konica Corporation, Tokyo, Japan

[21] Appl. No.: 170,673

[22] Filed: Dec. 20, 1993

Related U.S. Application Data

[63] Continuation of Ser. No. 951,577, Sep. 25, 1992, abandoned.

[30] Foreign Application Priority Data

Sep. 26, 1991 [JP] Japan .................. 3-277040
Feb. 28, 1992 [JP] Japan .................. 4-078305

[51] Int. Cl.$^6$ .................. C07K 14/47; C07K 14/435; C12N 9/76
[52] U.S. Cl. .................. 530/395; 530/380; 530/828; 530/829; 530/830; 435/24; 435/183; 435/213
[58] Field of Search .................. 530/385, 828, 829, 830, 530/380, 350; 514/8, 12, 21; 435/183, 213, 24

[56] References Cited

U.S. PATENT DOCUMENTS

| | | | |
|---|---|---|---|
| 4,916,117 | 4/1990 | Lezdey et al. | 514/8 |
| 5,008,242 | 4/1991 | Lezdey et al. | 514/8 |
| 5,093,316 | 3/1992 | Lezdey et al. | 514/8 |
| 5,114,917 | 5/1992 | Lezdey et al. | 514/8 |

OTHER PUBLICATIONS

Rozemuller et al. "Distribution Pattern and Functional State of αAntichymotrypsin in Plaques & Vascular Amyloid in Alzheimer's Disease" Acta Neuropath 82:200–207 Aug. 29, 1991.
Biorad Technical Bulleten Affagel 10 and 15: (No publication date given).
Votila et al (1981) J. Immunol. Methods 42: 11–15.
Kannazi et al (1986) Cancer Res. 46 2619–2626.
Sheer et al (1988) Concep Res 48: 6811–6818.
Imabori, K et al. (eds) (1990 "Biochemistry Dictionary", 2nd ed., p. 331 (Translation of relevant section).
Lee et al (1992) Cancer Immunol. Immunother, 35: 19–26.
Phamacia Technical Bulletin, "Separation Technique, File No. 110", (No publication date given).
Rozemuller et al (1991) Acta Neuropathologica 82: 200–207.
Rubin et al (1990) J. Biol. Chemistry 265 (2): 1199–1207.
Harlow et al (1988) "Antibodies: A Laboratory Manual", Cold Spring Harbor Press, Cold Spring Harbor, N.Y. pp. 553–612.

Primary Examiner—Michael G. Wityshyn
Assistant Examiner—Nancy J. Degen
Attorney, Agent, or Firm—Frishauf, Holtz, Goodman, Langer & Chick

[57] ABSTRACT

An isolated and purified substance called Acta having the following features: (a) a molecular weight of 60 kd to 70 kd in SDS-PAGE using 12.5% gel, (b) reacts with a monoclonal antibody which is secreted by hybridoma FERM BP-3482, (c) binds to chymotrypsin and (d) binds to DNA. Acta is used to diagnose cancer and Alzheimer's disease.

1 Claim, 8 Drawing Sheets

FIG.8

ACTA AND METHODS FOR DETECTING THE SAME

This application is a continuation of application Ser. No. 07/951,577, filed Sep. 25, 1992 (now abandoned).

BACKGROUND OF THE INVENTION

I. Field of the Invention

The present invention relates to a monoclonal antibodies useful for diagnosing cancers, inflammation and Alzheimer's disease and hybridomas producing the same. The present invention also relates to human $\alpha_1$-antichymotrypsin and methods for detecting or quantifying the human $\alpha_1$-antichymotrypsin.

II. Description of the Related Art

Human $\alpha_1$-antichymotrypsin (hereinafter also referred to as "ACT") is a glycoprotein which inhibits the protease activity of chymotrypsin, and is contained in body fluids such as blood. It is thought that the role of ACT is to protect the body by inhibiting the protease activities of bacteria and the like. It is known that the ACT levels in the body fluids of patients suffering from inflammation, cancers such as liver cancer, or Alzheimer's disease are higher than those of normal humans. Thus, it is now tried to diagnose these diseases by measuring the ACT levels in the body fluids.

The measurement of ACT is conventionally carried out by immunoassays or by measuring the inhibitor activity of ACT based on the inhibition of the chymotrypsin activity. However, the method in which the inhibitor activity is measured has drawbacks in that the operation is troublesome and the results are not accurate. As the immunoassays for measuring ACT, the SRID method and sandwich method which employ a polyclonal antibody have been carried out. However, as described later in detail, the present inventors discovered that ACT is a mixture of a plurality of ACTs. Thus, by the method in which the polyclonal antibody is employed, the total ACTs are measured since the polyclonal antibody reacts with the total ACTs. Therefore, although the measurement of the total ACTs has some diagnostic significance, the significance is less than that attained by measuring a specific ACT in the total ACTs.

SUMMARY OF THE INVENTION

Accordingly, an object of the present invention is to provide a monoclonal antibody by which a specific human ACT can be detected, that is useful for the diagnosis of cancers and Alzheimer's disease. Another object of the present invention is to provide a hybridoma producing the monoclonal antibody of the present invention. Still another object of the present invention is to provide a method for detecting or quantifying a specific human ACT.

During the study of the significance of measuring ACT, the present inventors discovered the ACT which was hitherto thought as a single substance is a heterogeneous mixture of different ACTs. Hereinafter, the total ACT (i.e., the mixture) is indicated by the plural form, ACTs. The expression of singular form, i.e., ACT (including a specific ACT, an ACT and the like) means an individual ACT in the total ACTs. The present inventors succeeded in obtaining a monoclonal antibody which specifically recognize a specific ACT. The present inventors further discovered that the measurement of the specific ACT has a very great significance in clinical diagnosis, thereby completing the present invention.

That is, the present invention provides a monoclonal antibody which specifically recognizes a specific human $\alpha_1$-antichymotrypsin among the total human $\alpha_1$-antichymotrypsins. The present invention also provides a hybridoma producing the monoclonal antibody of the present invention. The present invention further provides a method for detecting or quantifying the human $\alpha_1$-antichymotrypsin by an immunoassay utilizing immunological reaction between the human $\alpha_1$-antichymotrypsin and the corresponding monoclonal antibody of the present invention.

By the present invention, monoclonal antibodies each of which recognizes a corresponding specific human ACT, as well as the method for measuring the specific ACT utilizing the monoclonal antibody was provided. The method for measuring the specific ACT is useful for the diagnosis of inflammation, cancers and Alzheimer's disease. Particularly, by measuring a ratio of an amount of a specific ACT to an amount of another individual ACT is very useful for the diagnosis of Alzheimer's disease.

BRIEF DESCRIPTION OF THE DRAWINGS

FIG. 8 shows the amounts of substances (in terms of ACT) in cerebrospinal fluids from Alzheimer's disease patients, cerebrovascular dementia patients, and from normal humans, which were bound to each monoclonal antibody.

DETAILED DESCRIPTION OF THE PREFERRED EMBODIMENTS

Figure 1:
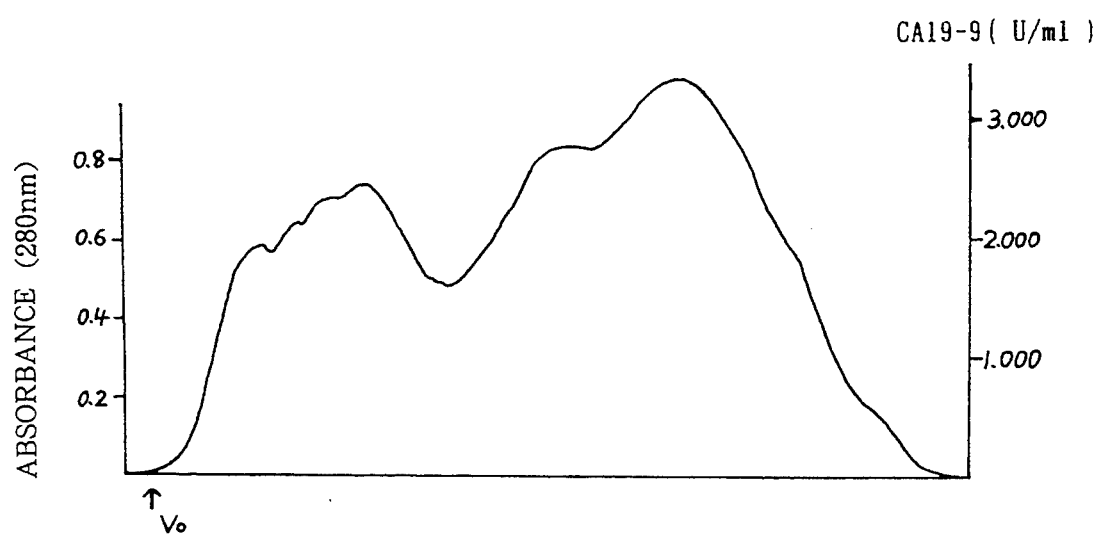
FIG. 1 shows the profile of the gel permeation chromatography of ascites from a liver cancer patient.

In the conventional methods, the total ACTs are measured and a part of the total ACTs alone cannot be measured, so that the diagnostic significance of the measurement of the part of the ACTs was not known. By the monoclonal antibody of the present invention, a specific region or a specific ACT among the total ACTs can be measured and the diagnostic significance thereof was discovered.

Recently, the usefulness of measuring ACTs in body fluids such as serum and cerebrospinal fluid for the diagnosis of Alzheimer disease was reported (Ann. Neurol., Vol. 28, pp561–567, 1990). However, since the total ACTs are measured, the quality of the diagnosis is not satisfactory. The present inventors discovered that the quality of the diagnosis is drastically promoted by measuring a part of the total ACTs by using the monoclonal antibody of the present invention.

Although the monoclonal antibodies of the present invention were obtained by preparing hybridomas by using proteins contained in ascites from a cancer patient as immunogens, the monoclonal antibodies may also be obtained from hybridomas prepared by using a body extract including the total ACTs, products purified therefrom, decomposition products thereof, synthesized polypeptides or genetically engineered products as immunogens.

Specific examples of the monoclonal antibodies of the present invention include AC-005, AC-006, AC-013, AC-606 and AC-065. The hybridomas producing these monoclonal antibodies, respectively, have been deposited with Fermentation Research Institute of Japan under the accession numbers FERM BP-3482 (deposited on Jul. 10, 1991), FERM BP-3776 (deposited on Mar. 2, 1992), FERM BP-3777 (deposited on Mar. 2, 1992), FERM BP-3775 (deposited on Mar. 2, 1992) and FERM BP-3778 (deposited on Mar. 2, 1992), respectively.

The monoclonal antibodies AC-006, AC-013, AC-606 and AC-065 have strong reactivities with the ACTs obtained by the conventional method (Arch. Biochem. Biophys., Vol. 225, pp.306–312, 1983), so that it is assumed that the epitopes of these monoclonal antibodies occupy a major part of the ACTs. Since the amounts of the ACTs measured by these monoclonal antibodies are clearly different from that obtained by the measurement using the conventional polyclonal antibody, the substances recognized by these monoclonal antibodies are different from the total ACTs. That is, it is considered that the ACT recognized by the monoclonal antibody of the present invention is a part of the total ACTs.

On the other hand, the reactivity of the monoclonal antibody AC-005 with the ACTs obtained by the conventional process is very small, so that it is assumed that the substance recognized by AC-005 is different from the known ACTs. The properties of the substance recognized by AC-005 were compared with those of ACTs. As described in detail in the examples later described, since the substance recognized by AC-005 has the following properties, it was proved that the substance is one having a major part that is common to the ACTs, so that it is a substance belonging to ACT substance group.

1) The substance has an inhibitory activity of chymotrypsin;
2) The substance binds to DNA; and
3) The monoclonal antibody prepared by using as an immunogen the substance purified by an affinity column to which AC-005 monoclonal antibody is fixed strongly reacts with ACT. This novel substance belonging to the ACT substance group, which has an epitope specific to AC-005 is hereinafter referred to as "Acta". Acta is clearly distinguished from the other ACTs by the fact that it has an epitope specific to AC-005. The content of Acta in the total ACTs is very small, which is usually 1/100 or less of the total ACTs.

The present inventors made it possible to detect a specific ACT in the ACT substance group by using the monoclonal antibody of the present invention. The desired ACT may be measured by an immunoassay by using the corresponding monoclonal antibody. The immunoassay which may be employed is not restricted and may be carried out by various conventional immunoassays including immunostaining methods, immunohistochemistry methods, EIAs, RIAs, FIAs, agglutination methods, competition methods, sandwich methods and the like. Among these, the sandwich methods are preferred. Especially, the sandwich method in which the monoclonal antibody is used as an immobilized antibody and a polyclonal antibody is used as a labelled antibody is preferred because the sensitivity and specificity of the assay are high. The monoclonal antibody may also be used as the labelled antibody.

Alternatively, since the ACTs bind to DNA, the sandwich immunoassay may be carried out by immobilizing DNA and using the monoclonal antibody of the present invention as the labelled antibody.

The five monoclonal antibodies AC-005, AC-006, AC013, AC-606 and AC-065 do not inhibit the binding abilities each other, so that the epitope of each of these monoclonal antibodies is different from each other. The results of the measurements of the ACTs in the body fluids by using monoclonal antibodies indicate the strong correlation between AC-006 and AC-013, so that it was proved that AC-006 and AC-013 recognize the same substance or very similar substances. The correlation of AC-606 and AC-065 is high, so that it was proved that AC-606 and AC-065 recognize the same substance or very similar substances.

The measurement of the specific ACT using the monoclonal antibody of the present invention is useful for clinical diagnosis. The diagnosis may be carried out by either immunohistochemistry or by testing body fluids. The diagnosis by using body fluids is preferred. Especially, the monoclonal antibody may preferably be applied to the diagnosis of various inflammations, cancers and neuropathies using blood (serum and plasma) and cerebrospinal fluid. It is most preferred to use the monoclonal antibody of the present invention for the diagnosis of cancers and Alzheimer's disease.

As described above, the present invention provides the specific human $\alpha_1$-antichymotrypsin recognized by the monoclonal antibody of the present invention. The specific human $\alpha_1$-antichymotrypsin recognized by the monoclonal antibody of the present invention may be obtained by preparing an affinity column in which the monoclonal antibody of the present invention is immobilized by a conventional method, applying, for example, ascites of a cancer patient to the column, washing the column with PBS and then eluting anti-chymotrypsin with 3M KSCN/PBS (see Example 2). The specific human $\alpha_1$-antichymotrypsin thus obtained may be used as an antigen for the preparation of the monoclonal antibody of the present invention.

The monoclonal antibodies of the present invention may be used for immunotherapy, missile therapy and the like.

The monoclonal antibodies of the present invention may be used as vaccines for inducing anti-idiotype antibodies.

The present inventors confirmed that by measuring the ratio of the amounts of two types of ACT, the quality of the diagnosis may be further promoted. For example, although it is known that the concentration of the total ACTs in the body fluids of patients suffering from Alzheimer's disease is larger than those of normal humans, the present inventors discovered that the sensitivity of the diagnosis is much more increased by the method utilizing the monoclonal antibody of the present invention. More particularly, although the level of Acta specifically recognized by AC-005 is apparently higher in the cerebrospinal fluid of patients suffering from Alzheimer's disease than in the normal humans so that the patients can be distinguished from normal humans, by measuring the ratio of the levels of Acta and a specific ACT recognized by the monoclonal antibody of the present invention, the sensitivity of the distinguishing of the Alzheimer's disease patients is further increased. Especially, measuring the ratio of Acta to the ACT recognized by AC-065 or by AC-606 is very effective for distinguishing patients suffering from Alzheimer's disease (AD) or cerebrovascular dementia (MID) from normal humans. Further, it was confirmed that by measuring the ratio of the total ACTs to the ACT recognized by AC-065 or AC-606, the sensitivity of the distinguishing is increased when compared to the case wherein the total ACTs alone are measured.

The present invention will now be described by way of examples thereof. It should be noted that the examples are presented for the illustration purpose only and should not be interpreted in any restrictive way.

EXAMPLE 1

Preparation of Monoclonal Antibodies

1) Preparation of Immunogen

Figure 2:
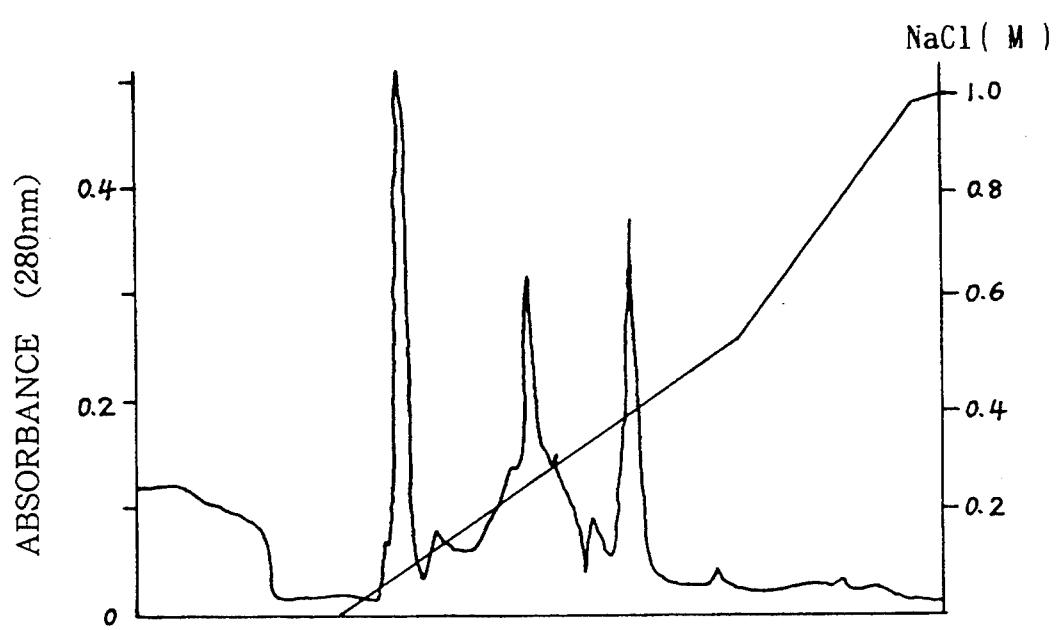
FIG. 2 shows the profile of the anion-exchange column chromatography which was conducted during the process of preparing an immunogen from ascites from a liver cancer patient.

Three hundred milliliters of ascites from a liver cancer patient was lyophilized and 200 ml of 0.6M perchloric acid was added thereto, followed by stirring the resulting mixture. The obtained supernatant was dialyzed against pure water and the obtained insoluble materials were separated and dried to obtain 372 mg of sample. The thus obtained sample was dissolved in 5 ml of 6M guanidine hydrochloride/PBS, and the resulting mixture was subjected to gel permeation chromatography on Sephacryl S-200HR column (5cm × 120 cm) commercially available from Pharmacia (FIG. 1). The fraction of the larger molecular weight in the two obtained fractions was dialyzed against PBS containing 8M urea (pH 8.5) and the resultant was subjected to an anion-exchange column chromatography on MonoQ column commercially available from Pharmacia (FIG. 2). The sharp peak eluted in the vicinity of 100 mM NaCl was dialyzed against PBS to prepare Sample-A, which was used as an immunogen.

The same procedure was repeated except that the starting material was 300 ml of serum from a normal human to prepare Sample-B.

2) Sensitization and Cell Fusion

One milliliter of Sample-A and equivolume of Freund's complete adjuvant were mixed and the resultant was emulsified. One hundred microliters of the thus obtained mixture was administered to the peritoneal cavity of a Balb/c mouse (8 weeks old, female). The immunization was carried out three times in the same manner as described above every three weeks.

Three days after the final immunization, the spleen was removed from the mouse and the spleen cells were separated into individual cells. The spleen cells were washed with RPMI 1640 medium. On the other hand, mouse myeloma cells X63.6.5.3 in the logarithmic phase were collected and washed with RPMI 1640 medium. The spleen cells ($2.5 \times 10^8$) and the mouse myeloma cells ($5 \times 10^7$) were mixed and cell fusion was carried out by using 50 wt % polyethylene glycol at 37° C. After removing the medium by centrifugation, 70 ml of RPMI 1640 medium containing 10 wt % fetal calf serum (FCS) was added to the cells and the cell suspension was placed in the wells of 96-well microtiter plates (7 plates) in an amount of 0.1 ml/well. On the next day, 0.1 ml of HAT medium (containing aminopterin, thymidine and hypoxanthine) was placed in each cell. Half volume of the HAT medium was replaced each 3 or 4 days. Three weeks after, growth of hybridomas was observed in most cells.

3) Selection of Hybridomas

The antibodies produced by the hybridomas were checked by ELISA. Sample-A or Sample-B was diluted with PBS to 5 μg/ml and the resultant was placed in the wells of 96-well microtiter plates in an amount of 50 μl per well, followed by immobilization of the sample overnight at 4° C. Then the wells were blocked with 1 wt % BSA/PBS, 50 μl of the culture supernatant was added to each well and the resultant was allowed to react at 37° C. for 1 hour. After washing the wells with PBS, the reaction product was reacted with HRP-labelled goat anti-mouse immunoglobulin antibody (commercially available from Cappel). To the reaction mixture, o-phenylenediamine as a coloring agent was added and the absorbance at 492 nm was measured. The hybridoma clones which exhibited stronger reactivity with Sample-A than with Sample-B were selected.

The obtained hybridomas were transferred to HT medium which is the same medium as HAT medium except that it does not contain aminopterin. The hybridomas were then transferred to RPMI 1640 medium containing 10 wt % FCS, and the hybridomas were cloned. That is, the hybridomas were diluted to a population density of 0.8 cell per well of 96-well microtiter plates and each hybridoma cell was cultured with $4 \times 10^5$ mouse thymus cells. Two weeks after the beginning of the culture, hybridomas which were producing antibodies were selected. The above-described operation was repeated to obtain stable hybridomas.

By the above-described procedure, three hybridomas AC-005, AC-006 and AC-013 were obtained. These hybridomas were deposited with Fermentation Research Institute of Japan under accession numbers FERM BP-3482, FERM P-12353 and FERM P-12354, respectively. The monoclonal antibodies AC-005, AC-006 and AC-013 produced by these hybridomas belong to class $IgG_1$.

EXAMPLE 2

Preparation of Monoclonal Antibodies - 2

1) Preparation of Immunogen

To AC-005 affinity column, 500 ml of ascites from a liver cancer patient was applied and the column was sufficiently washed with PBS. Thereafter, 3M KSCN/PBS was applied to the column so as to elute Acta which is the corresponding antigen of AC-005. The collected Acta was dialyzed against PBS and then the concentration of Acta was adjusted to 0.5 mg/ml.

2) Immunization and Cell Fusion

The thus prepared Acta was mixed and emulsified with Freund's complete adjuvant and 100 μl of the resulting emulsion was intraperitoneally administered to a Balb/c mouse (8 weeks old, female). One hundred microliters of the same emulsion was intravenously administered three times at two weeks' interval.

Three days after the final immunization, the spleen was removed from the mouse and the spleen cells were separated into individual cells. The spleen cells were washed with RPMI 1640 medium. On the other hand, mouse myeloma cells X63.6.5.3 in the logarithmic phase were collected and washed with RPMI 1640 medium. The spleen cells ($2 \times 10^8$) and the mouse myeloma cells ($4 \times 10^7$) were mixed and cell fusion was carried out by using 50 wt % polyethylene glycol at 37° C. After removing the medium by centrifugation, 60 ml of RPMI 1640 medium containing 10 wt % FCS was added to the cells and the cell suspension was placed in the wells of 96-well microtiter plates (6 plates) in an amount of 0.1 ml/well. On the next day, 0.1 ml of HAT medium was placed in each cell. Half volume of the HAT medium was replaced each 3 or 4 days. Three weeks after, growth of hybridomas was observed in most cells.

3) Selection of Hybridomas

Acta was diluted with PBS to a concentration of 1 μg/ml. Using the resultant as an immobilized antigen, the desired hybridomas were searched by ELISA in the same manner as in Example 1 and hybridomas were selected. As a result, two hybridomas AC-606 and AC-065 were obtained. These hybridomas were deposited with Fermentation Research Institute of Japan under the accession numbers of FERM P-12591 and FERM P-12590, respectively.

Both of the monoclonal antibodies produced by these hybridomas belong to class $IgG_{2b}$.

EXAMPLE 3

Characterization of Monoclonal Antibodies

1) Analysis of Antigens

The corresponding antigens of the obtained monoclonal antibodies were analyzed by electrophoresis and immunostaining with respect to Sample-A. More particularly, SDS-PAGE using 12.5 wt % gel and isoelectric focusing were carried out, followed by immunostaining. That is, Sample-A was blotted on a polyvinylidene fluoride (PVDF) membrane (commercially available from Millipore) and the membrane was blocked with 1 wt % BSA/PBS. Then each of the monoclonal antibodies was reacted with the blot. Thereafter, HRP-labelled goat anti-mouse immunoglobulin antibody was reacted with the reaction product. Detection of the label was carried out using Konica Immunostain Kit HRP (commercially available from Konica Corporation).

As a result, all of the monoclonal antibodies reacted with substances having molecular weights of 60 kd to 70 kd and pIs of 4.0 to 5.0.

Serum protein standards having the molecular weights and pIs around those mentioned above were checked for their reactivity with the monoclonal antibodies. As a result, it was proved that the monoclonal antibodies AC-006 and AC-013 react with ACT.

2) Specificities of Antibodies - 1

The reactivities of the monoclonal antibodies with Sample-A and ACT were examined by sandwich assay. That is, each monoclonal antibody was immobilized in the wells of 96-well microtiter plates by leaving an antibody solution in PBS with a concentration of 5 μg/ml in the wells and the wells were blocked. Then each sample (1 μg/ml) was added to the well and allowed to react. The immobilized antigens were reacted with HRP-labelled monoclonal antibodies. Then the immobilized HRP label was detected. The results are shown in Table 1.

TABLE 1

| Immobilized Antibody | Labelled Antibody | | | | | |
|---|---|---|---|---|---|---|
| | AC-005 | | AC-006 | | AC-013 | |
| | a | b | a | b | a | b |
| AC-005 | − | − | − | + | − | + |
| AC-006 | − | + | − | − | + | + |

TABLE 1-continued

| Immobilized Antibody | Labelled Antibody | | | | | |
|---|---|---|---|---|---|---|
| | AC-005 | | AC-006 | | AC-013 | |
| | a | b | a | b | a | b |
| AC-013 | − | + | + | + | − | − |

In Table 1, "a" shows the results of standard ACT and "b" shows the results of Sample-A. "−" means that the reaction did not occur and "+" means that the reaction occurred.

It can be seen from Table 1 that AC-006 and AC-013 have reactivities with ACT, that only one epitope corresponding to each monoclonal antibody exists in a substance, and that the epitopes corresponding to each monoclonal antibody are different from each other.

3) Specificity of Antibodies - 2

The Acta purified in Example 2, section 1) and ACT standard were checked for their reactivities with monoclonal antibodies AC-606 and AC-065 in the same manner as in Example 3, section 2). The results are shown in Table 2.

TABLE 2

| Immobilized Antibody | Labelled Antibody | | | | | | | |
|---|---|---|---|---|---|---|---|---|
| | AC-006 | | AC-013 | | AC-606 | | AC-065 | |
| | a | b | a | b | a | b | a | b |
| AC-005 | − | + | − | + | − | + | − | + |
| AC-606 | + | + | + | + | − | − | + | + |
| AC-065 | + | + | + | + | + | + | − | − |

In Table 2, "a" shows the results of standard ACT and "b" shows the results of Acta "−" means that the reaction did not occur and "+" means that the reaction occurred.

It can be seen from Table 2 that the epitopes corresponding to the five monoclonal antibodies of the present invention are different from each other, and that the monoclonal antibodies AC-606 and AC-065 produced by immunization with Acta have reactivities with ACT, so that Acta is a substance relating to ACT.

EXAMPLE 4

Analysis of Relationship Between Acta and ACT

1) Binding Ability to DNA

To an AC-005 affinity column, 500 ml of ascites from a liver cancer patient was applied and the column was washed with PBS. Acta was then eluted with 3M KSCN/PBS and isolated. The thus obtained Acta was then dialyzed against 10 mM phosphate buffer (pH 6.5, hereinafter referred to as "PB") and the resultant was applied to a DNA-cellulose column (commercially available from Pharmacia) according to the method of Abdullah et al (Archives of Biochemistry and Biophysics, Vol. 225, pp.306, 1983). After washing the column with PB, elution was carried out by using PB containing sodium chloride. As a result, Acta was eluted at NaCl concentration of 250 mM. The reactivity of the eluted fraction was checked by blotting the eluted fraction on a nitrocellulose membrane and by reacting the blot with POD-labelled AC-005.

As a result, it was proved that Acta has binding ability to DNA like ACT.

2) Protease Inhibitor Activity

Figure 3:
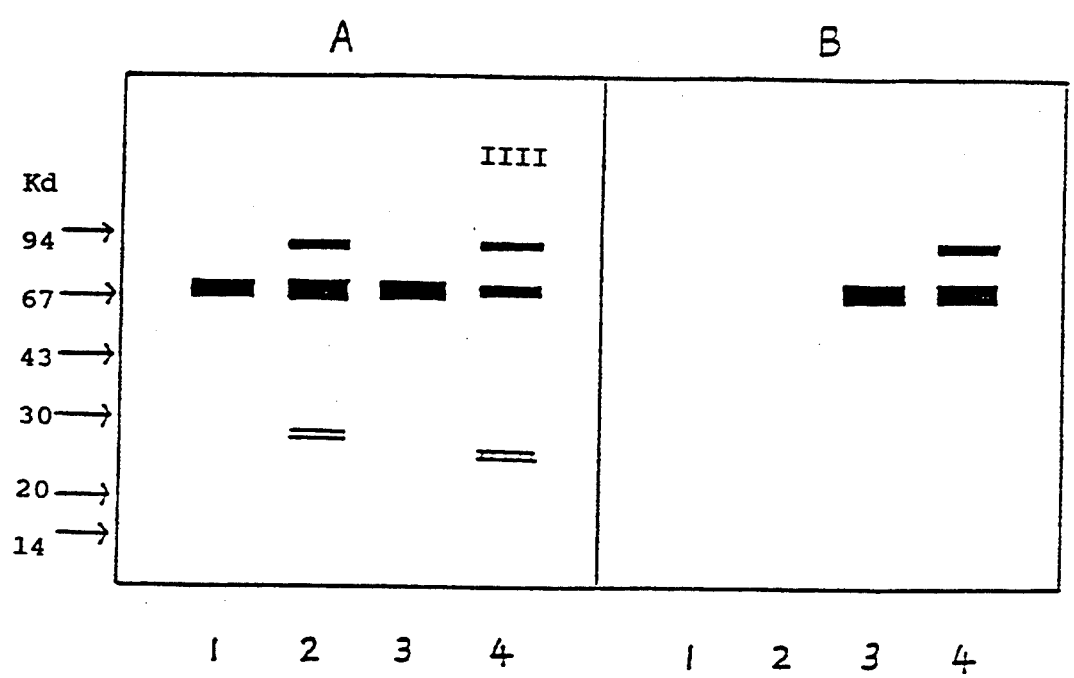
FIG. 3 schematically shows the results of a SDS-PAGE which was carried out for checking the protease inhibitor activity of Acta.

The protease inhibitor activity of Acta was examined by checking whether Acta has an ability to form a complex with a protease. That is, 5 ml of ascites from liver cancer patient and 5 ml of a solution containing 1 mg of bovine chymotrypsin (commercially available from Worthington Biochemical Corp.) in PBS were mixed and the resulting mixture was allowed to react at 37° C.

for 1 hour. The reaction mixture was then applied to an AC-005 affinity column and the column was sufficiently washed with PBS, followed by elution with 3M KSCN/PBS. The eluted solution was dialyzed against PBS and concentrated, and the resultant was analyzed by SDS-PAGE (FIG. 3). In FIG. 3, lane 1 shows the result of bovine chymotrypsin, lane 2 shows the result of the reaction mixture between bovine chymotrypsin and ACT, lane 3 shows the result of Acta and lane 4 shows the result of the above-mentioned concentrate. In FIG. 3, A shows the results obtained by staining the bands with silver and B shows the results obtained by immunostaining the bands with monoclonal antibody AC-005. As shown in FIG. 3, a band emerged in lane 4 at the same position as in lane 2 which shows the band of ACT/chymotrypsin complex (MW 90 kd), and this band showed reactivity with AC-005. From these results, it was proved that Acta has a protease inhibitor activity. From the results of Example 3—3) and of Example 4, it was proved that Acta belongs to the ACT substance group.

EXAMPLE 5

Figure 4:
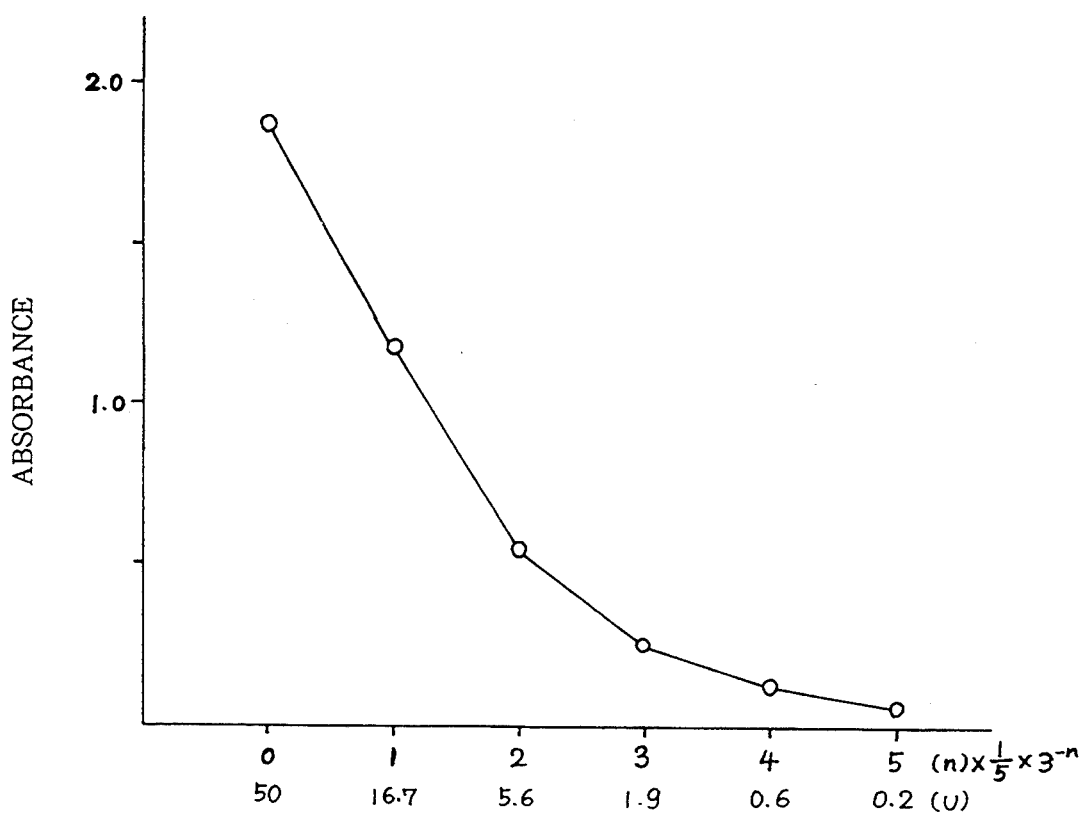
FIG. 4 is a calibration curve prepared for ascites from a liver cancer patient by using an immunoassay system utilizing AC-005.

A solution containing 10 μg/ml of monoclonal antibody AC-005 in PBS was placed in the wells of a 96-well microtiter plate in an amount of 50 μl/well, and the monoclonal antibody was immobilized overnight at 4° C. The wells were then treated with 1 wt % BSA/PBS overnight at 4° C. After washing the cells with PBS, 50 μl of the sample (ascites from a liver cancer patient) serially diluted from 5-fold with PBS was added to each well and the reaction was allowed to occur at room temperature for 2 hours. After washing the wells with PBS containing 0.05 wt % Tween-20, 50 μl of POD-labelled sheep anti-antichymotripsin antibody (commercially available from Binding Site, 1000-fold diluted with 1 wt % BSA/PBS) was added to each well and reaction was allowed to occur at room temperature for 1 hour. After washing the wells with PBS containing 0.05 wt % of Tween-20, 200 μl of citrate buffer (containing 0.02 wt % hydrogen peroxide, pH 5.0) containing 1 mg/ml of o-phenylenediamine was added to each well and the color reaction was allowed to occur at room temperature for 10 minutes. Fifty microliters of 9N sulfuric acid was added to each well to stop the color reaction and the absorbance at 492 nm was measured. Taking the amount of the substance in the ascites from the liver cancer patient, which was bound to AC-005 as 250U, a calibration curve was prepared (FIG. 4).

Figure 5:
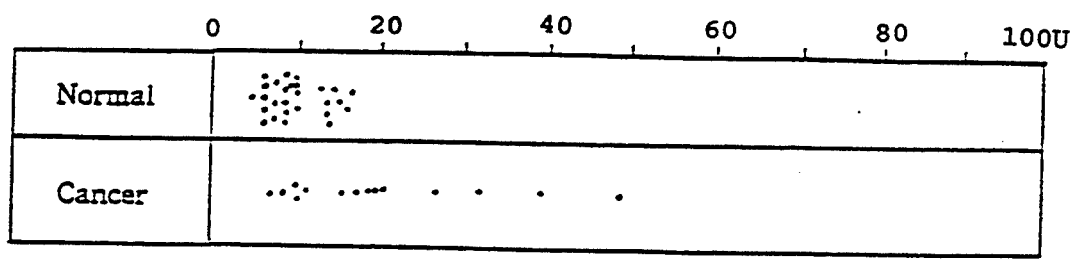
FIG. 5 shows U values of sera from normal humans and liver cancer humans.

Various samples (sera from 31 normal humans and sera from 16 cancer patients) were 10-fold diluted with 1 wt % BSA/PBS and were subjected to the measurement in the same manner just mentioned above to determine the U values of the samples from the calibration curve. The results are shown in FIG. 5. From FIG. 5, it can be seen that diagnosis of cancer can be carried out by this measuring system utilizing AC-005.

EXAMPLE 6

DNA (originated from bovine thymus, commercially available from Worthington Biochemical) was diluted with PBS to a concentration of 10 μg/ml and was immobilized in the wells of 96-well microtiter plates by being left to stand overnight at 4° C. Blocking was performed overnight at 4° C. using 1 wt % BSA/PBS. Standard ACT (commercially available from Attends Research) was diluted with 1 wt % BSA/PBS to a concentration of ACT of 10, 3.3, 1.1, 0.4 or 0 μg/ml. Each dilution of ACT was allowed to react with the DNA in the well at room temperature for 1 hour. The wells were washed with PB to remove the non-reacted materials. POD-labelled sheep anti-ACT antibody (commercially available from Binding Site) or POD-labelled AC-013 diluted with 1 wt % BSA/PB to a concentration of 1 μg/ml and 50 μl of the resulting dilution was added to each well. The mixture was incubated at room temperature for 1 hour. The wells were washed with PB and 0.2 ml of citrate buffer (pH 5.0) containing 0.02 wt % $H_2O_2$ and 1 mg/ml of o-phenylenediamine was added to each well. The color reaction was allowed to occur at room temperature for 10 minutes and then 50 μl of 9N sulfuric acid was added to each well to stop the color reaction. The absorbance at 492 nm of each well was measured to obtain a calibration curve with respect to the ACT concentration (Table 3).

Sera from 3 normal humans and sera from 3 liver cancer patients were 100-fold diluted and the above-described procedure was followed except that these diluted sera were used in place of the standard ACT. From the measured absorbances, the ACT levels were estimated based on the calibration curve obtained above (Table 4).

TABLE 3

| ACT Concentration (μg/ml) | | 0 | 0.4 | 1.1 | 3.3 | 10 |
|---|---|---|---|---|---|---|
| Absorbance | Polyclonal Antibody | 0.02 | 0.28 | 0.48 | 0.93 | 1.48 |
| | AC-013 | 0.03 | 0.21 | 0.49 | 1.10 | 1.83 |

TABLE 4

| | | ACT Concentration (μg/ml) | |
|---|---|---|---|
| | | Polyclonal Antibody | AC-013 |
| Normal Human Serum | A | 171 | 163 |
| | B | 125 | 132 |
| | C | 153 | 161 |
| Liver Cancer Patient Serum | A | 361 | 300 |
| | B | 586 | 572 |
| | C | 204 | 213 |

From these results, it can be seen that the quantification of ACT may be carried out easily with high reliability using this measuring system.

EXAMPLE 7

Fifty microliters of a solution containing 10 μg/ml of each monoclonal antibody in PBS was placed in each well of 96-well microtiter plates and the immobilization of the monoclonal antibody was carried out overnight at 4° C. Then 1 wt % BSA/PBS containing 0.05 wt % Tween-20 was added to the wells and the blocking was performed at 37° C. for 1 hour. After washing the wells with 0.05 wt % Tween-20/PBS, 50 μl of standard ACT diluted with 1 wt % BSA/PBS was added to each well and the reaction was allowed to occur at 37° C. for 1.5 hours. After washing the wells with 0.05 wt % Tween-20/PBS, 50 μl of POD-labelled sheep anti-ACT antibody was added to each well and the reaction was allowed to occur at 20° C. for 1.5 hours. After washing the wells with 0.05 wt % Tween-20/PBS, the color reaction was carried out in the same manner as in Example 5 to prepare calibration curves. Various samples (sera from 31 normal humans and sera from 26 gynecological cancer patients) diluted with 1 wt % BSA/PBS were subjected to the measurement in the same manner just mentioned above to determine the values in terms of the amount of the standard ACT (relative values). For comparison, the same procedure was repeated except that anti-ACT polyclonal antibody (commercially available from Binding Site) was used in place of the monoclonal antibodies. The dilutions of the sera were 50-fold for AC-005, 100-fold for AC-006, 400-fold for AC-013, 2000-fold for AC-606 and AC-065, and 50,000-fold for the polyclonal antibody.

Figure 6:
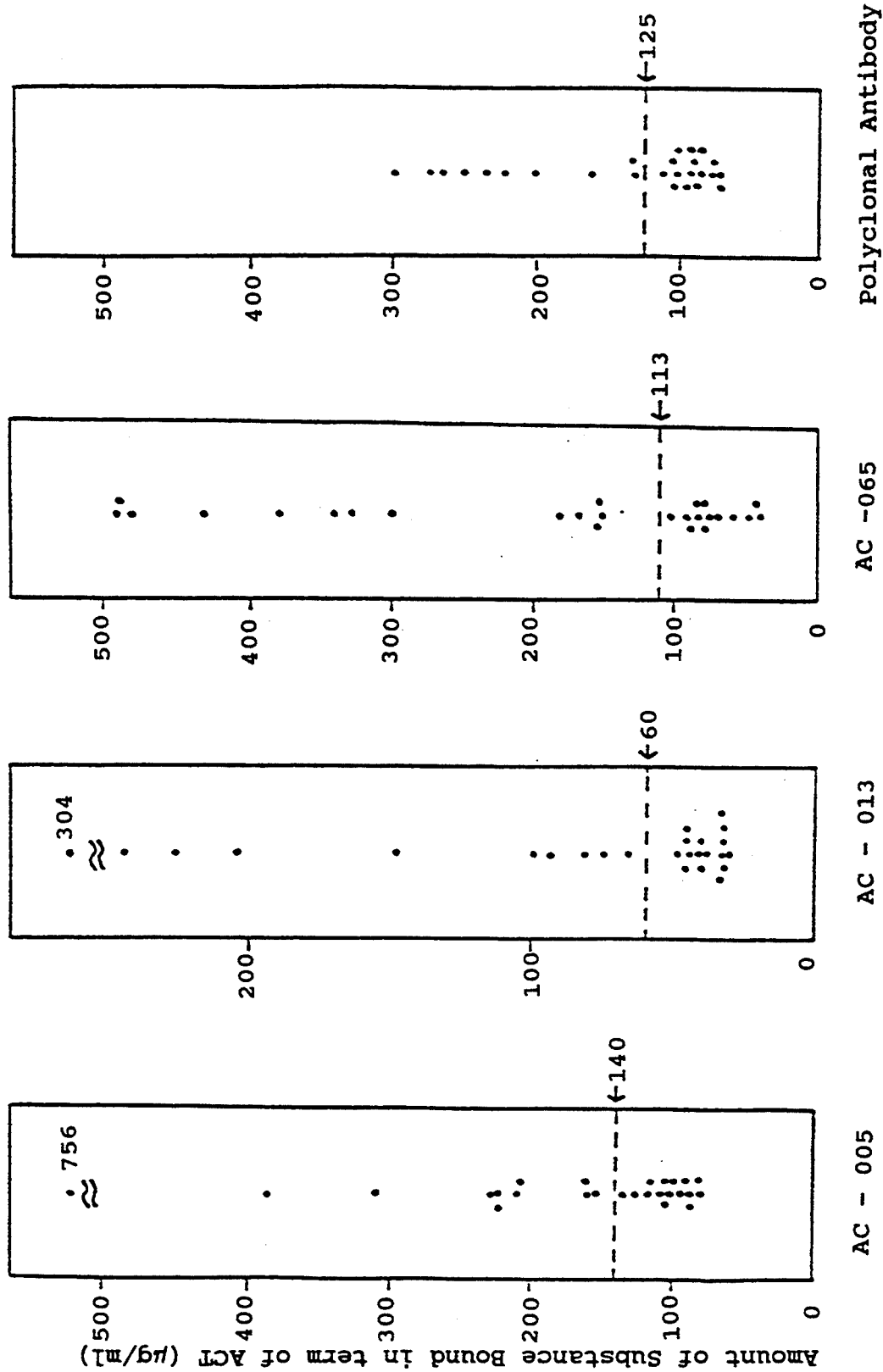
FIG. 6 shows the amounts of substances in sera from normal humans and cancer patients, which were bound to each monoclonal antibody in terms of ACT.

Setting the average value of the normal humans plus twice of the standard deviation as a cut off value, the positive rate was determined. The results are shown in FIG. 6 and Table 5. Since the results of AC-006 and AC013 were substantially identical and the results of AC606 and AC-065 were also substantially identical, only the results of AC-013 and AC-065 are shown. In FIG. 6, the cut off values are indicated by broken lines.

TABLE 5

| | Positive Rate of Cancer Patients (%) | Average of Normal Humans A (μg/ml) | Average of Cancer Patients B (μg/ml) | B/A (%) |
|---|---|---|---|---|
| Antibody | | | | |
| AC-005 | 42.3 | 96 | 175 | 182 |
| AC-013 | 38.5 | 31 | 83 | 268 |
| AC-065 | 50.0 | 72 | 192 | 267 |
| Polyclonal Antibody | 38.5 | 97 | 138 | 142 |

By the method of measuring the specific ACT according to the present invention by the monoclonal antibody, the positive rate is equal to or higher than the conventional method using the polyclonal antibody and the average value of the cancer patients to the average value of the normal humans is larger, so that the ability to distinguish the cancer patients is apparently higher than the conventional method.

EXAMPLE 8

By the same procedure as in Example 7, sera from 10 Alzheimer disease patients (hereinafter also referred to as "AD") were tested.

Figure 7:
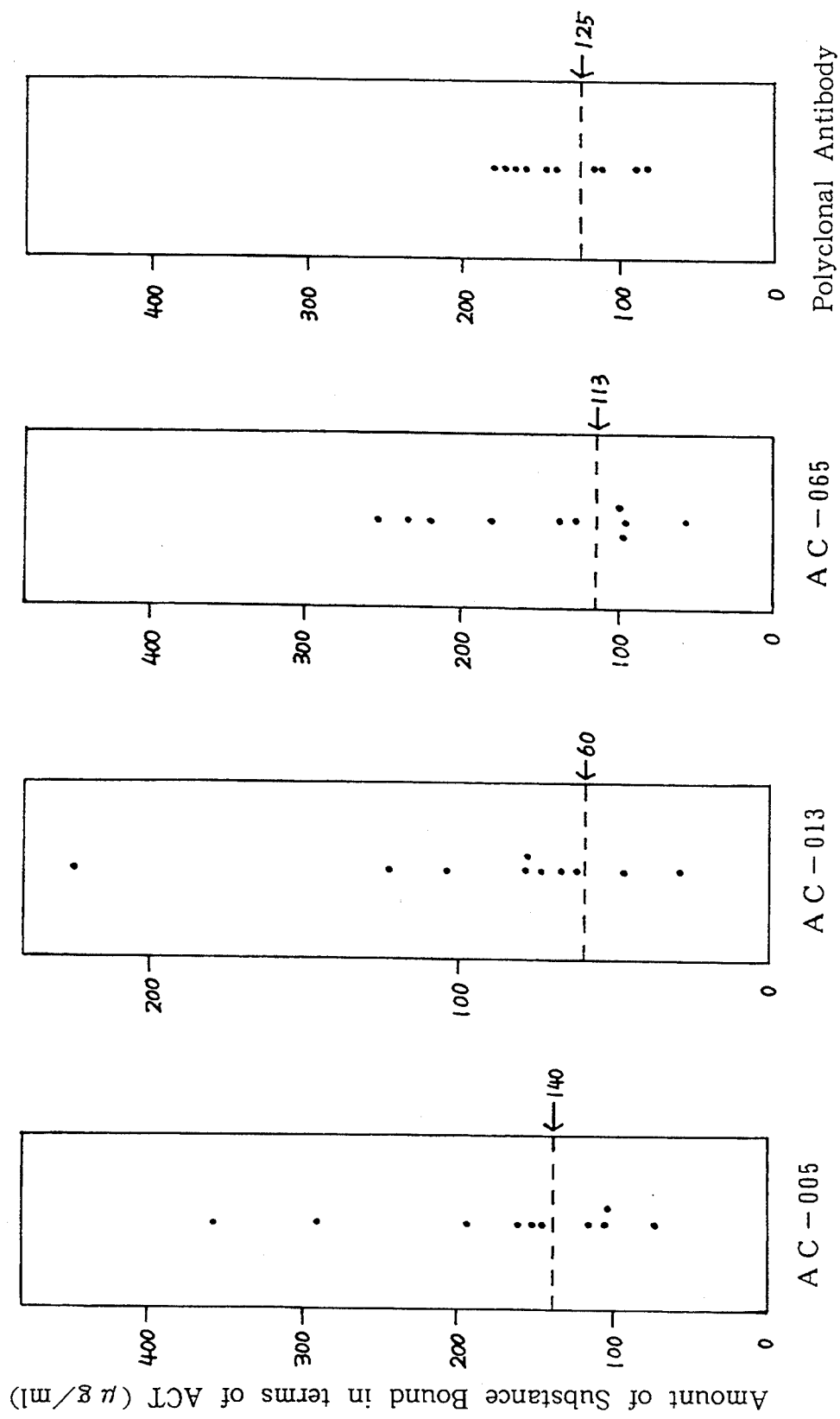
FIG. 7 shows the amounts of substances in sera from Alzheimer's disease patients, which were bound to each monoclonal antibody in terms of ACT.

The results are shown in FIG. 7 and Table 6. Since the results of AC-006 and AC-013 were substantially identical and the results of AC-606 and AC-065 were also substantially identical, only the results of AC-013 and AC-065 are shown. The positive rate was calculated using the cut off value employed in Example 7.

TABLE 6

| | Positive Rate of AD Patients (%) | Average of Normal Humans A (μg/ml) | Average of AD Patients B (μg/ml) | B/A (%) |
|---|---|---|---|---|
| Antibody | | | | |
| AC-005 | 60.0 | 96 | 170 | 177 |
| AC-013 | 80.0 | 31 | 89 | 287 |
| AC-065 | 60.0 | 72 | 150 | 208 |
| Polyclonal Antibody | 60.0 | 97 | 137 | 141 |

By the method of measuring the specific ACT according to the present invention by the monoclonal antibody, the positive rate is equal to or higher than the conventional method using the polyclonal antibody and the average value of the AD patients to the average value of the normal humans is larger, so that the ability to distinguish the AD patients is apparently higher than the conventional method.

EXAMPLE 9

By the same procedure as in Example 7, cerebrospinal fluids from 10 AD patients, 7 cerebrovascular dementia (hereinafter also referred to as "MID") patients and 7 normal humans were tested. The dilutions of the cerebrospinal fluids were 1.5-fold for AC-005, 3-fold for AC-006, 9-fold for AC-013, 50-fold for AC-606 and AC-065 and 500-fold for the polyclonal antibody.

Figure 8:
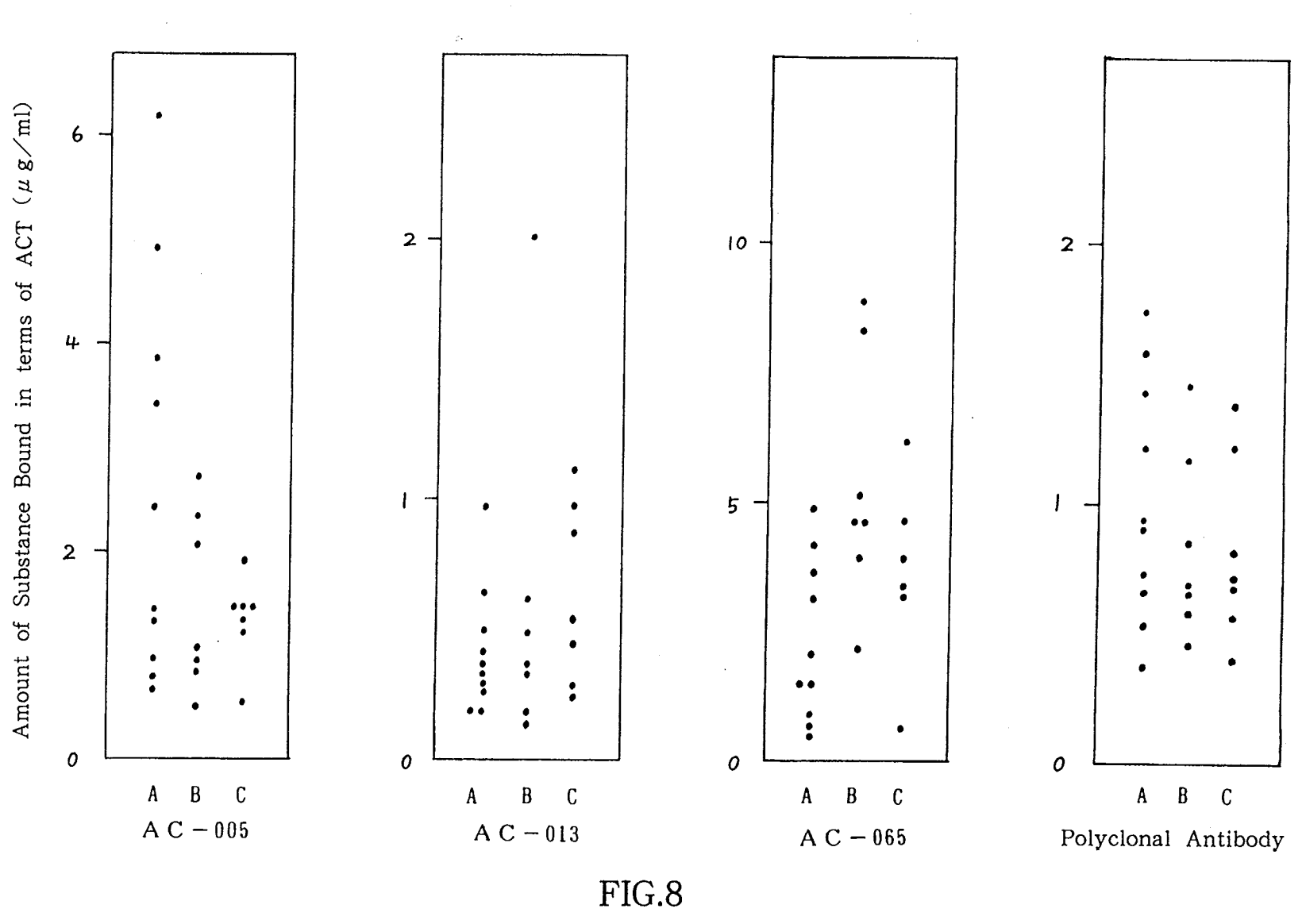

The results are shown in FIG. 8 and Table 7. Since the results of AC-006 and AC-013 were substantially identical and the results of AC-606 and AC-065 were also substantially identical, only the results of AC-013 and AC-065 are shown. In FIG. 8, "A" shows the results of AD patients, "B" shows the results of MID patients and "C" shows the results of normal humans.

TABLE 7

| | Average of Normal Humans A (μg/ml) | Average of AD Patients B (μg/ml) | Average of MID Patients (μg/ml) | B/A (%) |
|---|---|---|---|---|
| Antibody | | | | |
| AC-005 | 1.35 | 2.57 | 1.51 | 191 |
| AC-013 | 0.64 | 0.42 | 0.59 | 66 |
| AC-065 | 3.36 | 2.30 | 5.20 | 68 |
| Polyclonal Antibody | 0.82 | 0.98 | 0.83 | 120 |

The measuring system utilizing AC-005 exhibited a clear difference between normal humans and AD patients, so that the utility of this system for the diagnosis of AD was confirmed.

On the other hand, in the measuring system utilizing AC-006, AC-013, AC-606 or AC-065, the samples from AD patients exhibited somewhat lower values than those from normal humans.

EXAMPLE 10

Based on the results obtained in Example 9, the ratio of the value obtained by using AC-005 to the value obtained by using AC-013 (AC-006) or AC-065 (AC-606) was calculated. The results are shown in Table 8.

TABLE 8

| Combination of Antibodies | Average of MID Patients A (μg/ml) | Average of AD Patients B (μg/ml) | B/A (%) |
|---|---|---|---|
| AC-005 Alone | 1.51 | 2.57 | 170 |
| AC-005/AC-013 | 3.58 | 6.42 | 179 |
| AC-005/AC-065 | 0.28 | 1.34 | 476 |
| Polyclonal Antibody Alone | 0.83 | 0.98 | 118 |
| Polyclonal Antibody/AC-013 | 2.15 | 2.52 | 117 |
| Polyclonal Antibody/AC-065 | 0.17 | 0.53 | 312 |
| AC-065/Polyclonal Antibody | 1.80 | 2.43 | 135 |

As can be seen from Table 8, by calculating the ratio of AC-005/AC-013 (AC-006) or AC-005/AC-065 (AC606), especially, the AC-005/AC-013 (AC-006) ratio, the ability to distinguish AD from MID is promoted than that based the results of AC-005 alone. Similarly, by calculating the ratio of polyclonal antibody/AC-065 (or AC-606), the ability to distinguish AD from MID is promoted than that based on the results of the polyclonal antibody alone.

We claim:

1. An isolated and purified substance called Acta and having the following features:

(a) a molecular weight of 60 kd to 70 kd in SDS-PAGE using 12.5% gel,
(b) reacts with a monoclonal antibody which is secreted by hybridoma FERM BP-3482,
(c) binds to chymotrypsin and
(d) binds to DNA.

* * * * *